(12) United States Patent
Kim et al.

(10) Patent No.: US 10,478,323 B2
(45) Date of Patent: Nov. 19, 2019

(54) BIODEGRADABLE STENT AND SHAPE MEMORY EXPANDING METHOD THEREFOR

(71) Applicant: Suntech Co., Ltd., Seoul (KR)

(72) Inventors: Hyungil Kim, Seoul (KR); Hyun Hee Han, Seoul (KR)

(73) Assignee: SUNTECH CO., LTD., Seoul (KR)

( * ) Notice: Subject to any disclaimer, the term of this patent is extended or adjusted under 35 U.S.C. 154(b) by 0 days.

(21) Appl. No.: 15/329,957

(22) PCT Filed: Dec. 8, 2015

(86) PCT No.: PCT/KR2015/013405
§ 371 (c)(1),
(2) Date: Jan. 27, 2017

(87) PCT Pub. No.: WO2016/093601
PCT Pub. Date: Jun. 16, 2016

(65) Prior Publication Data
US 2017/0266026 A1    Sep. 21, 2017

(30) Foreign Application Priority Data

Dec. 8, 2014 (KR) .................. 10-2014-0175249

(51) Int. Cl.
*A61F 2/91* (2013.01)
*A61F 2/958* (2013.01)
(Continued)

(52) U.S. Cl.
CPC ................ *A61F 2/958* (2013.01); *A61F 2/91* (2013.01); *A61L 31/06* (2013.01); *A61L 31/14* (2013.01);
(Continued)

(58) Field of Classification Search
CPC .... A61F 2/958; A61F 2/95; A61F 2210/0004; A61F 2210/0014; A61F 2230/0069;
(Continued)

(56) References Cited

U.S. PATENT DOCUMENTS 5,836,965 A * 11/1998 Jendersee ............... A61F 2/958
604/103.07
7,886,419 B2   2/2011 Huang et al.
(Continued)

FOREIGN PATENT DOCUMENTS

KR    10-2014-0038941 A    3/2014
WO    2014/064183 A1    5/2014

OTHER PUBLICATIONS

International Search Report dated Apr. 29, 2016 from International Application No. PCT/KR2015/013405, 4 pages with English translation.
(Continued)

*Primary Examiner* — Paul B Prebilic
(74) *Attorney, Agent, or Firm* — MH2 Technology Law Group, LLP

(57) ABSTRACT

The present invention relates to a biodegradable stent and a shape memory extending method thereof. According to an exemplary embodiment of the present invention, radial force of a biodegradable stent may be largely increased through the shape memory extending method of the biodegradable stent and the number of cracks may be decreased after crimping and stent inflation.

11 Claims, 14 Drawing Sheets

(51) Int. Cl.
*A61L 31/06* (2006.01)
*A61L 31/14* (2006.01)
*A61L 31/16* (2006.01)
*A61F 2/95* (2013.01)

(52) U.S. Cl.
CPC ............ *A61L 31/148* (2013.01); *A61L 31/16* (2013.01); *A61F 2002/9522* (2013.01); *A61F 2210/0004* (2013.01); *A61F 2210/0014* (2013.01); *A61L 2400/16* (2013.01)

(58) Field of Classification Search
CPC .. A61F 2250/001; A61L 31/14; A61L 31/148; A61L 31/06; A61L 2400/16
See application file for complete search history.

(56) References Cited

U.S. PATENT DOCUMENTS

| | | | |
|---|---|---|---|
| 8,099,849 B2 | 1/2012 | Gale et al. | |
| 8,187,396 B2 | 5/2012 | Parker | |
| 9,931,787 B2* | 4/2018 | Harrington | B23K 26/38 |
| 2003/0055482 A1* | 3/2003 | Schwager | A61F 2/91 |
| | | | 623/1.11 |
| 2003/0083732 A1* | 5/2003 | Stinson | A61F 2/91 |
| | | | 623/1.15 |
| 2005/0049670 A1* | 3/2005 | Jones | A61F 2/91 |
| | | | 623/1.12 |
| 2006/0069424 A1* | 3/2006 | Acosta | A61F 2/91 |
| | | | 623/1.12 |
| 2007/0129784 A1 | 6/2007 | Lendlein et al. | |
| 2007/0283552 A1* | 12/2007 | Gale | A61F 2/91 |
| | | | 29/515 |
| 2009/0088829 A1 | 4/2009 | Wang et al. | |
| 2010/0274349 A1* | 10/2010 | Lord | A61F 2/91 |
| | | | 623/1.16 |
| 2012/0073733 A1* | 3/2012 | Ngo | A61F 2/915 |
| | | | 156/196 |
| 2012/0296406 A1* | 11/2012 | Minion | A61F 2/07 |
| | | | 623/1.11 |
| 2014/0025161 A1* | 1/2014 | Stankus | A61L 31/148 |
| | | | 623/1.19 |
| 2014/0277331 A1 | 9/2014 | Ngo et al. | |
| 2014/0309722 A1 | 10/2014 | Igaki et al. | |
| 2017/0119564 A1* | 5/2017 | Huang | A61F 2/958 |

OTHER PUBLICATIONS

Extended European Search Report dated Jun. 1, 2018 from European Application No. 15868032.2, 9 pages.

\* cited by examiner

[Figure 1]
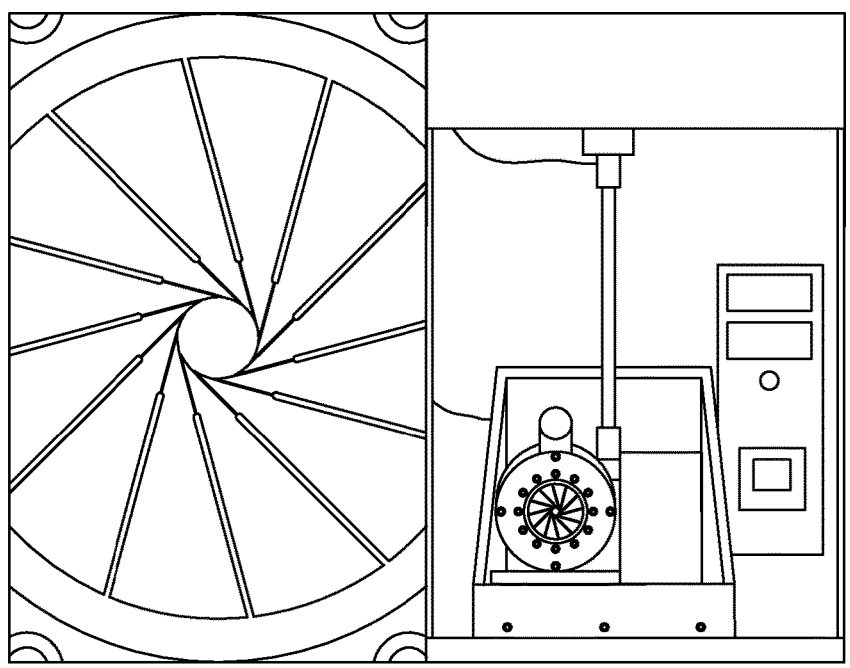

[Figure 2]
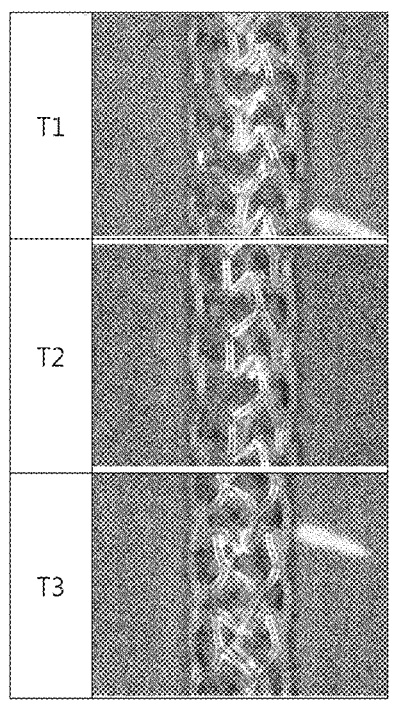

[Figure 3]
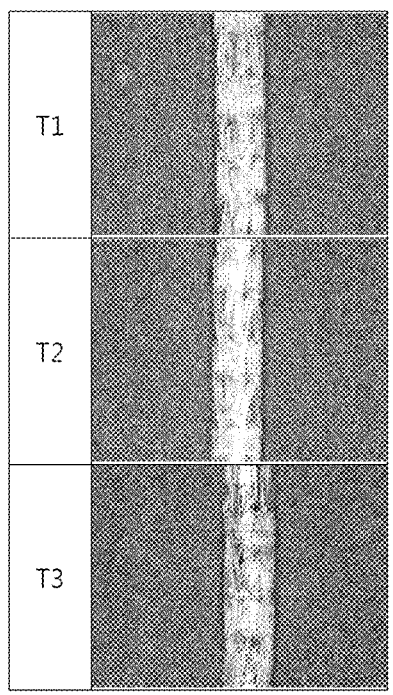

[Figure 4]
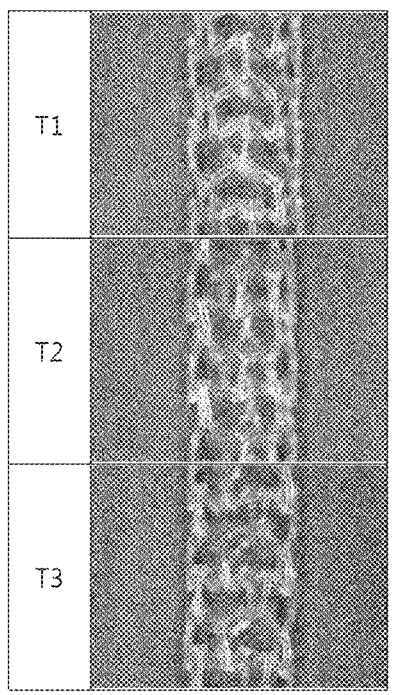

[Figure 5]
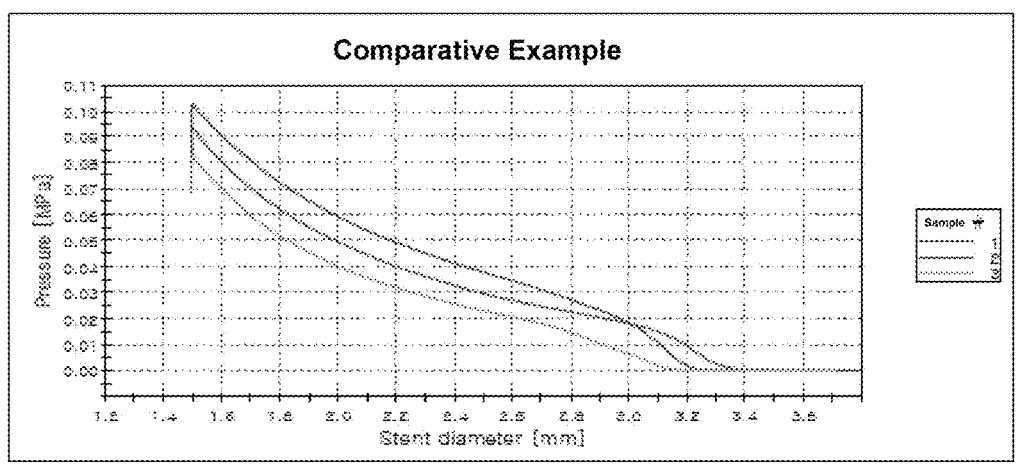

[Figure 6]
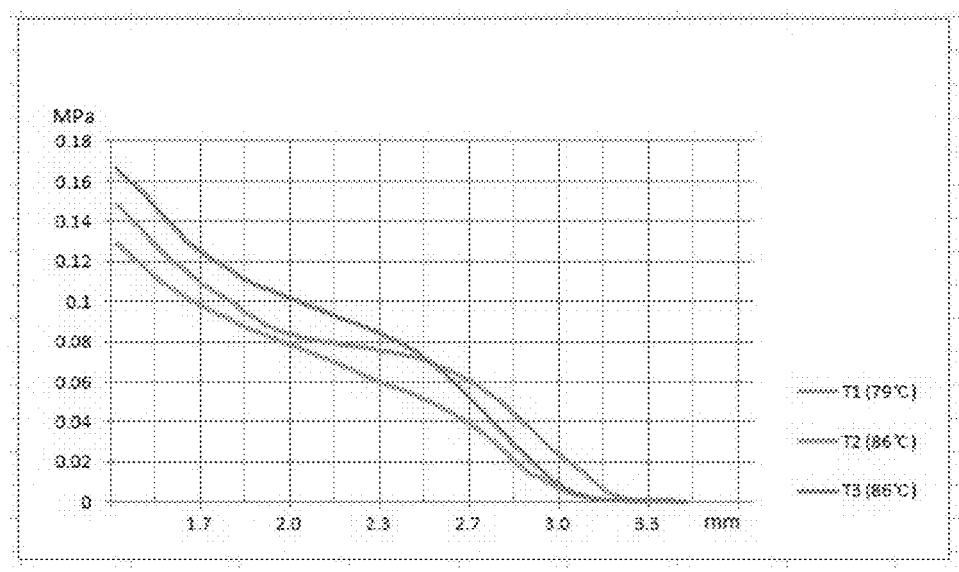

[Figure 7]
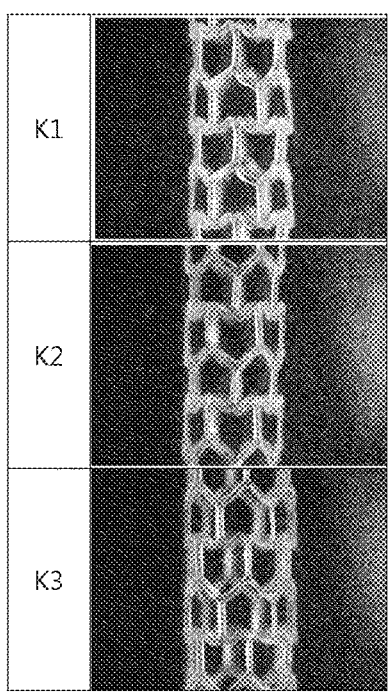

[Figure 8]
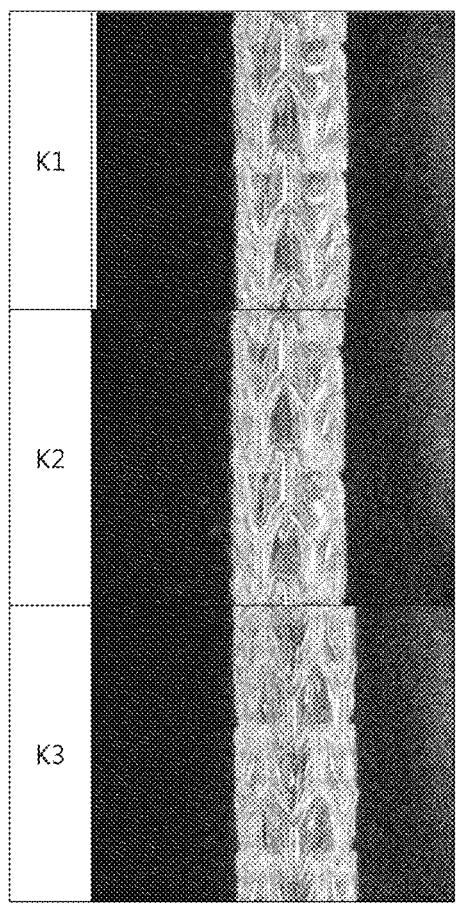

[Figure 9]
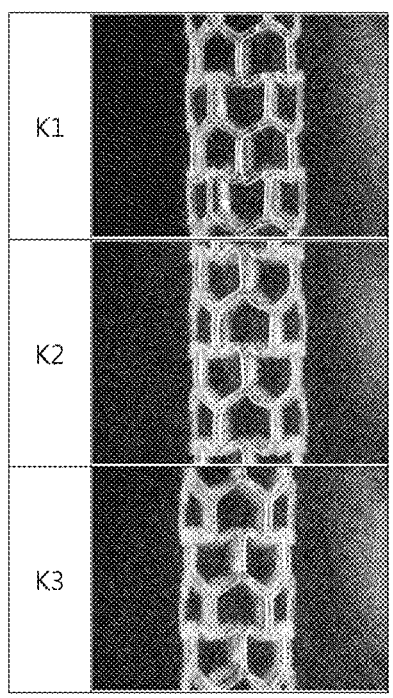

[Figure 10]
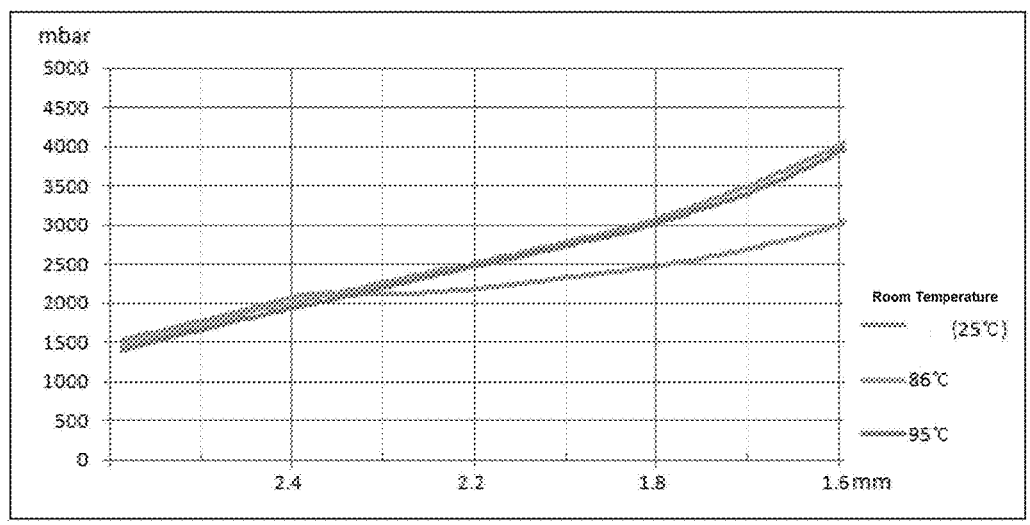

[Figure 11]
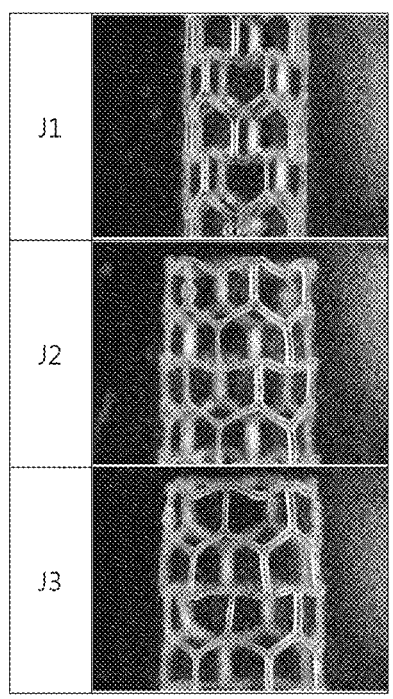

[Figure 12]
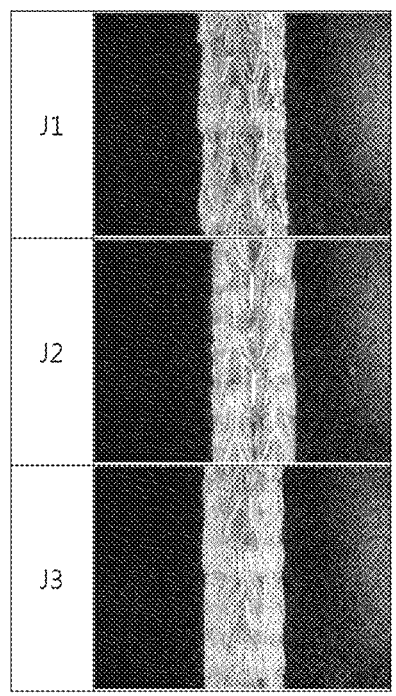

[Figure 13]
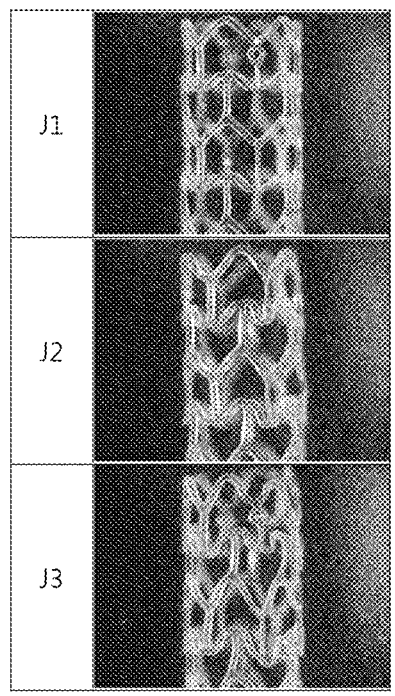

[Figure 14]
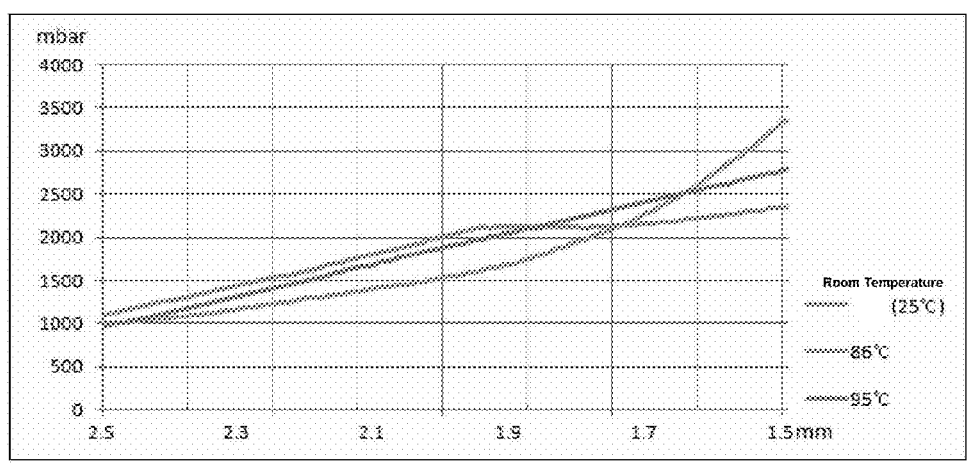

US 10,478,323 B2

BIODEGRADABLE STENT AND SHAPE MEMORY EXPANDING METHOD THEREFOR

TECHNICAL FIELD

This application is a U.S. National Stage application of PCT/KR2015/013405 filed 8 Dec. 2015, which claims priority to and the benefit of Korean Patent Application No. 10-2014-0175249 filed in the Korean Intellectual Property Office on Dec. 8, 2014, the entire contents of which are incorporated herein by reference.

The present invention relates to a biodegradable stent and a shape memory extending method thereof.

BACKGROUND ART

In general, a stent is an expandable medical prostheses and is used in body vessels of a person for various medical purposes.

Examples thereof include intravascular stents for treating stenoses, and stents for maintaining urinary, biliary, tracheobronchial, esophageal, and renal tracts, and an opening of inferior vena cava.

In general, the stent is transported to a treatment site through the body vessels by using a transporting device that maintains the stent in a contracted state.

In percutaneous transluminal angioplasty, implantable endoprosthesis, that is, the stent is introduced through the transporting device and transferred to the treatment site through vessel conduits. After the stent accesses the treatment site, the stent is generally mechanically expanded and thus expanded in the vessel conduits by the aid of an inflatable balloon. Thereafter, the transporting device is retreated from the stent and removed from a patient. The stent as an implant exists in a conduit at the treatment site.

DETAILED DESCRIPTION OF THE INVENTION

Technical Problem

The present invention has been made in an effort to provide a biodegradable stent having an excellent mechanical strength and a shape memory extending method thereof.

Technical Solution

An exemplary embodiment of the present invention provides a shape memory extending method of a biodegradable stent, including:

providing a stent made of a biodegradable polymer on an external surface of a balloon of a first balloon catheter;

extending an outer diameter of the stent by applying pressure to the balloon of the first balloon catheter;

providing a biodegradable stent of which the outer diameter is extended on the external surface of the balloon of a second balloon catheter; and reducing the outer diameter of the stent of which the outer diameter is extended by applying the pressure to the balloon of the second balloon catheter.

Further, another exemplary embodiment of the present invention provides a biodegradable stent of which a shape memory is extended according to the shape memory extending method.

Advantageous Effects

According to the present invention, an effect of shape memory extension can be achieved, in which radial force of a biodegradable stent largely increases through a shape memory extending process and the number of cracks decreases after a balloon extends and an outer diameter of the biodegradable stent is controlled and extended by means of a crimper while applying pressure to the balloon and a molecule array state of a polymer is changed.

A balloon catheter may be divided into three types according to balloon compliance. A balloon of which a change rate from a minimum diameter to a maximum diameter of the balloon is in the range of 5 to 10% is a non-compliant balloon, a balloon of which the change rate from the minimum diameter to the maximum diameter of the balloon is in the range of 15 to 30% is a semi-compliant balloon, and a balloon of which the change rate from the minimum diameter to the maximum diameter of the balloon is in the range of 50 to 600% is a compliant balloon. In the present invention, when the compliant balloon in which a change of an outer diameter of the balloon is not limited during shape memory extension is used, the stent can be uniformly extended by using a balloon which is not folded and an effect of an increase in radial force and a decrease in the number of cracks is improved through uniform extension of the stent.

BRIEF DESCRIPTION OF DRAWINGS

FIG. 1 is a diagram schematically illustrating an equipment for measuring radial force of a stent according to an exemplary embodiment of the present invention.

FIG. 2 is a diagram schematically illustrating an external appearance of a biodegradable stent after a shape memory extension process by using a nylon made semi-compliant balloon as an exemplary embodiment of the present invention.

FIG. 3 is a diagram schematically illustrating the external appearance of the biodegradable stent after the shape memory extension process and a crimping process by using the nylon made semi-compliant balloon as an exemplary embodiment of the present invention.

FIG. 4 is a diagram schematically illustrating the external appearance of a biodegradable stent after the shape memory extension process, the crimping process, and stent inflation by using a nylon made semi-compliant balloon as an exemplary embodiment of the present invention.

FIG. 5 is a diagram schematically illustrating a measurement result of radial force of the biodegradable stent according to a comparative example of the present invention.

FIG. 6 is a diagram schematically illustrating the measurement result of the radial force of the biodegradable stent after a shape memory extension process, a crimping process, and stent inflation by using a nylon made semi-compliant balloon according to an exemplary embodiment of the present invention.

FIG. 7 is a diagram schematically illustrating an external appearance of the biodegradable stent after the shape memory extension process by using a nylon made compliant balloon as an exemplary embodiment of the present invention.

FIG. 8 is a diagram schematically illustrating the external appearance of the biodegradable stent after the shape memory extension process and the crimping process by using the nylon made compliant balloon as an exemplary embodiment of the present invention.

FIG. 9 is a diagram schematically illustrating the external appearance of the biodegradable stent after the shape memory extension process, the crimping process, and the stent inflation by using the nylon made compliant balloon as an exemplary embodiment of the present invention.

FIG. 10 is a diagram schematically illustrating a measurement result of radial force of the biodegradable stent after the shape memory extension process, the crimping process, and the stent inflation by using the nylon made compliant balloon as an exemplary embodiment of the present invention.

FIG. 11 is a diagram schematically illustrating the external appearance of the biodegradable stent after the shape memory extension process by using a polyurethane made compliant balloon as an exemplary embodiment of the present invention.

FIG. 12 is a diagram schematically illustrating the external appearance of the biodegradable stent after the shape memory extension process and the crimping process by using the polyurethane made compliant balloon as an exemplary embodiment of the present invention.

FIG. 13 is a diagram schematically illustrating the external appearance of the biodegradable stent after the shape memory extension process, the crimping process, and the stent inflation by using the polyurethane made compliant balloon as an exemplary embodiment of the present invention.

FIG. 14 is a diagram schematically illustrating the measurement result of the radial force of the biodegradable stent after the shape memory extension process, the crimping process, and the stent inflation by using the polyurethane made compliant balloon as an exemplary embodiment of the present invention.

BEST MODE

Hereinafter, the present invention will be described in more detail.

A biodegradable stent which is formed in a cylindrical shape by using a biodegradable polymer material having a shape memory characteristic is shape-memorized with a diameter-enlarged size having an outer peripheral diameter supporting a blood vessel from the inside. When the stent is implanted into the blood vessel, the stent supports the blood vessel from the inside by maintaining a diameter-enlarged state to the shape-memorized size. This type of stent is mounted on a catheter, inserted into the blood vessel together with the catheter, and implanted to a lesion portion in a vasculature.

However, the stent which is diameter-enlarged to the size to support the blood vessel from the inside is mounted on the catheter in a diameter-reduced state to a size having a sufficiently smaller outer peripheral diameter than the shape-memorized size in order to enable smooth insertion into the blood vessel.

Therefore, the stent formed by using the biodegradable polymer material is transported up to the lesion portion which is an implantation location in the blood vessel and thereafter, is immediately diameter-enlarged by using extension force of a balloon to rapidly extend by injection of an extension medium so as to be diameter-enlarged to the size to support an inner wall of the blood vessel.

As described above, the stent formed by using the biodegradable polymer material which is diameter-enlarged by using the extension force of the balloon is mounted on the balloon mounted while being folded on a front end of the catheter and transported to the implantation portion in the blood vessel together with the balloon, in a diameter-reduced state. In addition, when the stent is transported to a desired implantation location of the blood vessel, the extension medium is supplied to the balloon to be extended and thus rapidly diameter-enlarged to the size to support the blood vessel from the inside and implanted to the lesion portion. When the stent made of the biodegradable polymer material is just diameter-enlarged, the extension medium is extracted from the balloon and even after the balloon is reduced, a flow path of blood in the blood vessel is secured by supporting the portion into which the stent is implanted from the inside.

The present inventors have researched a method for extending a shape memory of a biodegradable stent and completed the present invention.

A shape memory extending method of a biodegradable stent according to an exemplary embodiment of the present invention includes: providing a stent made of a biodegradable polymer on an external surface of a balloon of a first balloon catheter; extending an outer diameter of the stent by applying pressure to the balloon of the first balloon catheter; providing the stent of which the outer diameter is extended on the external surface of the balloon of a second balloon catheter; and reducing the outer diameter of the stent of which the outer diameter is extended by applying the pressure to the balloon of the second balloon catheter.

In the present invention, the stent may be formed in a cylindrical shape to configure one path from one side to the other side by combining a plurality of tubular body forming elements in which a series of consecutive filament bodies made of the biodegradable polymer are bent so that a straight part and a bent part are sequentially consecutive. The size of the stent may be appropriately selected according to the vasculature of the implanted blood vessel of a living body. For example, when the stent is configured as a stent implanted into the blood vessel such as the coronary, the stent may be formed in a tubular shape in which an outer peripheral diameter may be 2 to 6 mm and the length of the stent is 10 to 40 mm, as the size of the stent implanted in the blood vessel. That is, the stent may be formed with a size to have the outer peripheral diameter to support the blood vessel in which the stent is implanted from the inside.

In the present invention, the biodegradable polymer may be a synthetic biodegradable polymer or a natural biodegradable polymer.

The synthetic biodegradable polymer may be one polymer or a copolymer or a mixture of selected from polyglycolide, polylactide, poly p-dioxanone, polycaprolactone, trimethylene carbonate, polyhydroxyalkanoates, polypropylene fumarate, polyortho esters, other polyester, polyanhydride, polyphosphazenes, polyalkylcianoacrylatepoloxamers, and polyamino L-tyrosine.

Further, the natural biodegradable polymer may be one material or one or more mixtures selected from modified polysaccharides, oxidized cellulose, gelatin, and collagen.

In the present invention, the stent made of the biodegradable polymer may be a stent acquired by laser-cutting a biodegradable polymer tube.

In the present invention, each of the first balloon catheter and the second balloon catheter may be independently provided in crimping equipment.

In the present invention, the extending of the outer diameter of the stent may be performed in a temperature range less than a melting point of the biodegradable polymer of a room temperature or higher, a temperature range equal to or higher than a glass transfer temperature of the biodegradable polymer and less than the melting point, and the like. In more detail, the temperature range may be 25 to 180° C., 55 to 180° C., and the like, but is not limited only thereto.

Further, the extending of the outer diameter of the stent may be performed by extending the outer diameter of the balloon by applying the pressure to the balloon of the balloon catheter. The pressure may be 1 to 350 psi (0.06 to 23.8 atm) and be in a range of 1 atmospheric pressure or higher and a rupture pressure of the balloon catheter or lower, but is not limited only thereto.

In the present invention, an execution time of the extending of the outer diameter of the stent may be 1 second or more and 10 minutes or less, but is not limited thereto.

In the present invention, the reducing of the outer diameter of the stent may be performed in the temperature range of 37° C. to 80° C.

In the present invention, the outer diameter of the stent may be changed by 105 to 500% based on the outer diameter of the initial stent through the shape memory extending process.

In the present invention, the outer diameter of the stent may be changed by 10 to 50% based on the outer diameter of the stent which is maximally enlarged through the crimping process.

In the present invention, the crimping equipment, the balloon catheter, and the like may adopt equipment known in the art, and the like. The crimping equipment is equipment that constantly reduces the outer diameter of the stent while applying the pressure to the balloon by mounting the stent on the balloon catheter. The balloon catheter may be divided into three types according to a balloon compliance. A balloon of which a change rate from a minimum diameter to a maximum diameter of the balloon is in the range of 5 to 10% is a non-compliant balloon, a balloon of which the change rate from the minimum diameter to the maximum diameter of the balloon is in the range of 15 to 30% is a semi-compliant balloon, and a balloon of which the change rate from the minimum diameter to the maximum diameter of the balloon is in the range of 50 to 600% is a compliant balloon. In the present invention, when the compliant balloon in which a change of an outer diameter of the balloon is not limited is used, the stent may be mounted while the balloon is not folded and an effect of an increase in radial force of the biodegradable stent and a decrease in the number of cracks of the biodegradable stent is improved during crimping and balloon extension through uniform extension of the balloon and the biodegradable stent.

In the present invention, each of the first balloon catheter and the second balloon catheter may be independently a compliant balloon catheter or semi-compliant balloon catheter. In particular, the first balloon catheter may be the compliant balloon catheter or the second balloon catheter may be the semi-compliant balloon catheter. Further, the first balloon catheter may be the compliant balloon catheter in which the balloon is not folded or the second balloon catheter may be the semi-compliant balloon catheter in which the balloon catheter is folded.

In the present invention, as stent sterilization, radiation sterilization, ethylene oxide sterilization, nitrogen gas sterilization, and the like may be used.

Further, an exemplary embodiment of the present invention provides a biodegradable stent of which a shape memory is extended according to the shape memory extending method. The biodegradable stent is subjected to processes including tube extrusion, laser cutting, shape memory extension, crimping, drug coating, and the like. However, after a biodegradable polymer is extruded with a tube, a molecular array of a biodegradable tube is irregular and the molecular array of a stent which is laser-cut is also is also irregular. The molecular array in the stent is reoriented based on a portion where a strain of the biodegradable stent is high through shape memory extension to improve mechanical strength. Further, crack formation may be reduced during the crimping process and the stent inflation through the shape memory extension.

The stent of the present invention as an expandable medical prosthesis may serve to maintain a shape of a body vessel by being implanted into the body vessel of a person for various medical purposes.

The stent of the present invention may be used as intravascular stents for treating stenoses, and stents for maintaining urinary, biliary, tracheobronchial, esophageal, and renal tracts, and an opening of inferior vena cava.

According to the present invention, radial force of the biodegradable stent may be significantly increased and the number of cracks may be decreased through the shape memory extension process. This may be an effect of the shape memory extension in which a molecular array state of the biodegradable polymer is changed by controlling and extending an outer diameter with a crimper while applying pressure to the balloon.

MODE FOR INVENTION

Hereinafter, the present invention will be described in more detail through Examples. However, the following Examples are used for exemplifying the present invention and the scope of the present invention is not limited thereto.

EXAMPLES

[Biodegradable Stent in which Shape Memory is Extended by Using Nylon Made Semi-Compliant Balloon]

A comparative example of crimping a stent in which a poly L lactic-acid tube having a thickness of 150 μm is laser-cut to a strut width of 150 μm and an example of adding the shape memory process by using a folded semi-compliant balloon were separately performed and thereafter, the radial force and the cracks were observed.

Orders and conditions of a general process (comparative example) in the related art and a shape memory extending process according to an exemplary embodiment of the present invention are shown in Table 1 given below.

TABLE 1

|  |  | Shape memory | Crimping |
|---|---|---|---|
| Comparative example | S1 | None | 48° C. |
|  | S2 |  | Diameter: 1.1 mm |
|  | S3 |  | Rate: 0.02 mm/s |
| Example | T1 | 79° C. expansion rate 0.02 mm/s, holding time 10 sec | Protective sheath |
|  | T2 | 79° C. expansion rate 1 mm/s, holding time 0 sec |  |
|  | T3 | 86° C. expansion rate 1 mm/s, holding time 0 sec |  |

In the Example, the shape memory extending process, the crimping process, and the balloon extending process were sequentially performed and in the comparative example, the processes except for the shape memory extending process were performed similarly to the Example.

<Shape Memory Extending Process>

1) A gas valve connected to crimping equipment was opened and an equipment power supply was turned on.

2) Diameter calibration was performed while waiting for setting a temperature of a blade of a crimper.

3) A spiral portion was strongly fixed to an end of a handle of a balloon catheter by connecting the spiral portion with an inlet of a nitrogen line of the crimping equipment without a leakage portion.

4) A part where the balloon of the catheter is positioned was positioned at a catheter fixing bar at a front portion of the crimping equipment and the catheter was fixed to the bar similarly thereto.

5) The stent was positioned between metallic markers positioned at both sides inside the balloon by inserting a stent of which the shape memory will be extended into a balloon portion of the fixed catheter and thereafter, the stent was slowly pushed into the blade of the crimping equipment together with the catheter while being careful so as to prevent the stent from moving.

6) The shape memory extending process was performed under the following condition.

TABLE 2

|   | Type | 0 Diameter | 1 Diameter | 2 Diameter | 4 Pressure | 5 Diameter | 6 Pressure |
|---|---|---|---|---|---|---|---|
| T1 | Dia. Or Press (mm or psi) | 14.00 | 7.00 | 2.10 | ON | 3.3 | OFF |
|  | Speed or press (s or psi) | 3.00 | 3.00 | 1.00 | 50 | 0.02 |  |
|  | Time(s) |  | 2 | 180 | 60 | 10 | 3 |
| T2 | Dia. Or Press (mm or psi) | 14.00 | 7.00 | 2.10 | ON | 3.3 | OFF |
|  | Speed or press (mm or psi) | 3.00 | 3.00 | 1.00 | 50 | 1.00 |  |
|  | Time(s) |  | 2 | 180 | 60 | 0 | 3 |
| T3 | Dia. Or Press (mm or psi) | 14.00 | 7.00 | 2.10 | ON | 3.3 | OFF |
|  | Speed or press (mm or psi) | 3.00 | 3.00 | 1.00 | 50 | 1.00 |  |
|  | Time(s) |  | 2 | 180 | 60 | 0 | 3 |

T1 and T2 were performed at 79° C. and T3 was performed at 86° C. and in T1, a velocity at which the outer diameter of the stent is extended from 2.1 mm to 3.3 mm was extended to 0.02 mm/sec and in T2 and T3, the velocity during the stent inflation was extended to 1 mm/sec.

<Crimping Process>

1) The gas valve connected to the crimping equipment was opened and the equipment power supply was turned on.

2) The diameter calibration was performed while waiting for setting the temperature of the blade of the crimper.

3) The spiral portion was strongly fixed to the end of the handle of the catheter by connecting the spiral portion with the inlet of the nitrogen line of the crimping equipment without the leakage portion.

4) The part where the balloon of the catheter is positioned was positioned at the catheter fixing bar at the front portion of the crimping equipment and the catheter was fixed to the bar similarly thereto.

5) The stent was positioned between metallic markers positioned at both sides inside the balloon by inserting a stent to be crimped into a balloon portion of the fixed catheter and thereafter, the stent was slowly pushed into the blade of the crimping equipment together with the catheter while being careful so as to prevent the stent from moving.

6) The protective sheath was mounted after performing the crimping process that compresses the stent up to a diameter of 1.1 mm.

<Stent Inflation>

1) The catheter on which the stent to be inflated into warm water (38° C.) was mounted was fixed.

2) The stent was immersed in the water for 1 minute.

3) The a balloon inflator is filled with warm water to be connected with the balloon catheter.

4) The pressure was increased by 2 atmospheric pressure per 5 seconds.

5) When the pressure reaches nominal pressure suitable for a specification of the balloon catheter, the inflation stopped for 10 seconds.

6) After the pressure was removed, water stained in the stent was wiped with a wiper and a state was observed.

7) The stent of which observation has been completed was dried in a vacuum desiccator for 24 hours and thereafter, a next test was performed.

<Measurement of Radial Force>

The radial force of the inflated stent was measured by a stent radial force measuring jig and a tensile strength tester (UTM).

The radial force measuring equipment is schematically illustrated in FIG. 1.

1) A jig for measuring stent radiation force was installed in the tensile strength tester.

2) Calibration was performed in order to adjust a diameter of a radiation force measurer with a system.

3) Length information of the stent was input into the system and thereafter, the stent was contracted up to 1.5 mm and a graph thereof was recorded. The result is illustrated in FIGS. 5 and 6.

As an exemplary embodiment of the present invention, the external appearance of the stent after the shape memory extending process is schematically illustrated in FIG. 2 given below.

Further, as an exemplary embodiment of the present invention, the external appearance of the stent after the crimping process is schematically illustrated in FIG. 3 given below.

In addition, as an exemplary embodiment of the present invention, the external appearance of the stent after the stent inflation is schematically illustrated in FIG. 4 given below.

Moreover, a change of the outer diameter (mm) for each process of the example of the present invention is shown in Table 3 given below.

TABLE 3

|  | Before shape memory extension | After shape memory extension | Crimping | Stent inflation |
|---|---|---|---|---|
| T1 | 2.10 | 3.30 | 1.10 | 3.08 |
| T2 | 2.10 | 3.30 | 1.10 | 2.97 |
| T3 | 2.10 | 3.30 | 1.10 | 2.97 |

Further, the radial force measurement results of the example and the comparative example of the present invention are shown in Table 4 given below.

TABLE 4

|  |  | Radial force at 1.5 mm (mbar) |  |
|---|---|---|---|
| Comparative example | S1 | 934 | Average 927 |
|  | S2 | 1,025 |  |
|  | S3 | 823 |  |

TABLE 4-continued

|  |  | Radial force at 1.5 mm (mbar) |  |
|---|---|---|---|
| Example | T1 | 1,479 | Average 1,485 |
|  | T2 | 1,291 |  |
|  | T3 | 1,685 |  |

[Biodegradable Stent in which Shape Memory is Extended by Using Nylon Made Compliant Balloon]

The shape memory process was performed with respect to the stent in which the poly L lactic-acid tube having the thickness of 150 μm is laser-cut to the strut width of 150 μm at temperatures of different respective conditions by using the unfolded compliant balloon and thereafter, the radial force and the cracks were observed.

The order and the condition of the shape memory extending process according to an exemplary embodiment of the present invention are shown in Table 5 given below.

TABLE 5

|  |  | Shape memory | Crimping |
|---|---|---|---|
| Example | K1 | 25° C. expansion rate 1 mm/s, holding time 0 sec | 58° C. Diameter: 1.72 mm Rate: 1.00 mm/s |
|  | K2 | 86° C. expansion rate 1 mm/s, holding time 0 sec |  |
|  | K3 | 95° C. expansion rate 1 mm/s, holding time 0 sec |  |

In the Example, the shape memory extending process was performed as described below.

<Shape Memory Extending Process>
1) The gas valve connected to the crimping equipment was opened and the equipment power supply was turned on.
2) The diameter calibration was performed while waiting for setting the temperature of the blade of the crimper.
3) The spiral portion was strongly fixed to the end of the handle of the catheter by connecting the spiral portion with the inlet of the nitrogen line of the crimping equipment without the leakage portion.
4) The part where the balloon of the catheter is positioned was positioned at the catheter fixing bar at the front portion of the crimping equipment and the catheter was fixed to the bar similarly thereto.
5) The stent was positioned between metallic markers positioned at both sides inside the balloon by inserting a stent of which the shape memory will be extended into a balloon portion of the fixed catheter and thereafter, the stent was slowly pushed into the blade of the crimping equipment together with the catheter while being careful so as to prevent the stent from moving.
6) The shape memory extending process was performed under the following condition.

TABLE 6

|  |  | Step | | | | | |
|---|---|---|---|---|---|---|---|
|  |  | 0 Diameter | 1 Diameter | 2 Diameter | 4 Pressure | 5 Diameter | 6 Pressure |
| Type | | | | | | | |
| K 1, 2, 3 | Dia. Or Press (mm or psi) | 14.00 | 7.00 | 2.30 | ON | 3.30 | OFF |
|  | Speed or press (mm or psi) | 3.00 | 3.00 | 1.00 | 220 | 1.00 |  |
|  | Time(s) |  | 2 | 180 | 60 | 0 | 3 |

In the conditions of K1, K2, and K3, all processes except for a temperature were similarly performed.

<Crimping Process>
The stent was mounted on the semi-compliant balloon catheter and the crimping was performed as follows.
1) The gas valve connected to the crimping equipment was opened and the equipment power supply was turned on.
2) The diameter calibration was performed while waiting for setting the temperature of the blade of the crimper.
3) The spiral portion was strongly fixed to the end of the handle of a new catheter by connecting the spiral portion with the inlet of the nitrogen line of the crimping equipment without the leakage portion.
4) The part where the balloon of the catheter is positioned was positioned at the catheter fixing bar at the front portion of the crimping equipment and the catheter was fixed to the bar similarly thereto.
5) The stent was positioned between metallic markers positioned at both sides inside the balloon by inserting a stent to be crimped into a balloon portion of the fixed catheter and thereafter, the stent was slowly pushed into the blade of the crimping equipment together with the catheter while being careful so as to prevent the stent from moving.
6) The protective sheath was mounted after performing the crimping process that compresses the stent up to a diameter of 1.8 mm.

<Stent Inflation>
1) The catheter on which the stent to be inflated into warm water (38° C.) was mounted was fixed.
2) The stent was immersed in the water for 1 minute.
3) The inflator was filled with warm water to be connected with the catheter.
4) The pressure was increased by 2 atmospheric pressure per 5 seconds.
5) When the pressure reaches the nominal pressure suitable for each specification of the catheter, the inflation stopped for 10 seconds.
6) After the pressure was removed, water stained in the stent was wiped with a wiper and the state was observed.
7) The stent of which observation has been completed was dried in the vacuum desiccator for 24 hours and thereafter, the next test was performed.

<Measurement of Radial Force>
The radial force of the prepared stent was measured by the stent radial force measuring jig and the tensile strength tester (UTM).

The radial force measuring equipment is schematically illustrated in FIG. 1.

1) The jig for measuring the stent radiation force was installed in the tensile strength tester.
2) The calibration was performed in order to adjust the diameter of the radiation force measurer with the system.
3) The length information of the stent was input into the system and thereafter, the stent was contracted up to 1.5 mm and the graph thereof was recorded. The result is shown in FIG. 10.

As an exemplary embodiment of the present invention, the external appearance of the stent after the shape memory extending process is schematically illustrated in FIG. 7.

Further, as an exemplary embodiment of the present invention, the external appearance of the stent after the crimping process is schematically illustrated in FIG. 8 given below.

In addition, as an exemplary embodiment of the present invention, the external appearance of the stent after the balloon inflation is schematically illustrated in FIG. 9 given below.

Moreover, the change of the outer diameter (mm) for each process of the Example of the present invention is shown in Table 7 given below.

TABLE 7

| | Before shape memory extension | After shape memory extension | Crimping | Balloon inflation |
|---|---|---|---|---|
| K1 | 2.30 | 3.30 | 1.80 | 3.30 |
| K2 | 2.30 | 3.30 | 1.80 | 3.34 |
| K3 | 2.30 | 3.30 | 1.80 | 3.35 |

Further, the radial force measurement results of the example and the comparative example of the present invention are shown in Table 8 given below.

TABLE 8

| | | Radial force at 1.5 mm (mbar) |
|---|---|---|
| Example | K1 | 3676 |
| | K2 | 4134 |
| | K3 | 3939 |

[Biodegradable Stent in which Shape Memory is Extended by Using Polyurethane Made Compliant Balloon]

The shape memory process was performed with respect to the biodegradable stent in which the poly L lactic-acid tube having a thickness of 150 μm is laser-cut to a strut width of 150 μm at respective different temperatures by using the unfolded polyurethane made compliant balloon and thereafter, the radial force and the cracks were observed.

The order and the condition of the shape memory extending process according to an exemplary embodiment of the present invention are shown in Table 9 given below.

TABLE 9

| | | Shape memory | Crimping |
|---|---|---|---|
| Example | J1 | 25° C. expansion rate 0.5 mm/s, holding time 3 sec | 58° C. Diameter: 1.72 mm Rate: 1.00 mm/s |
| | J2 | 86° C. expansion rate 0.5 mm/s, holding time 3 sec | |
| | J3 | 95° C. expansion rate 0.5 mm/s, holding time 3 sec | |

In the Example, the shape memory extending process was performed as described below.

<Shape Memory Extending Process>

1) The gas valve connected to the crimping equipment was opened and the equipment power supply was turned on.
2) The diameter calibration was performed while waiting for setting the temperature of the blade of the crimper.
3) The spiral portion was strongly fixed to the end of the handle of the catheter by connecting the spiral portion with the inlet of the nitrogen line of the crimping equipment without the leakage portion.
4) The part where the balloon of the catheter is positioned was positioned at the catheter fixing bar at the front portion of the crimping equipment and the catheter was fixed to the bar similarly thereto.
5) The stent was positioned between metallic markers positioned at both sides inside the balloon by inserting a stent of which the shape memory will be extended into a balloon portion of the fixed catheter and thereafter, the stent was slowly pushed into the blade of the crimping equipment together with the catheter while being careful so as to prevent the stent from moving.
6) The shape memory extending process was performed under the following condition.

TABLE 10

| | | Step | | | | | |
|---|---|---|---|---|---|---|---|
| | | 0 | 1 | 2 | 4 | 5 | 6 |
| Type | | Diameter | Diameter | Diameter | Pressure | Diameter | Pressure |
| J 1, 2, 3 | Dia. Or Press (mm or psi) | 14.00 | 7.00 | 3.45 | ON | 5.0 | OFF |
| | Speed or press (mm or psi) | 3.00 | 3.00 | 1.00 | 15 | 0.50 | |
| | Time(s) | | 2 | 180 | 60 | 3 | 3 |

In the conditions of shape memory extending processes of J1, J2, and J3, all processes except for the temperature were similarly performed.

<Crimping Process>

The stent was mounted on the semi-compliant balloon catheter and the crimping was performed as follows.

1) The gas valve connected to the crimping equipment was opened and the equipment power supply was turned on.

2) The diameter calibration was performed while waiting for setting the temperature of the blade of the crimper.

3) The spiral portion was strongly fixed to the end of the handle of the new catheter by connecting the spiral portion with the inlet of the nitrogen line of the crimping equipment without the leakage portion.

4) The part where the balloon of the catheter is positioned was positioned at the catheter fixing bar at the front portion of the crimping equipment and the catheter was fixed to the bar similarly thereto.

5) The stent was positioned between metallic markers positioned at both sides inside the balloon by inserting a stent to be crimped into a balloon portion of the fixed catheter and thereafter, the stent was slowly pushed into the blade of the crimping equipment together with the catheter while being careful so as to prevent the stent from moving.

6) The protective sheath was mounted after performing the crimping process that compresses the stent up to a diameter of 1.8 mm.

<Stent Inflation>

1) The catheter on which the stent to be inflated into warm water (38° C.) was mounted was fixed.

2) The stent was immersed in the water for 1 minute.

3) The inflator is filled with warm water to be connected with the catheter.

4) The pressure was increased by 2 atmospheric pressure per 5 seconds.

5) When the pressure reaches the nominal pressure suitable for the specification of the catheter, the inflation stopped for 10 seconds.

6) After the pressure was removed, water stained in the stent was wiped with the wiper and the state was observed.

7) The stent of which observation has been completed was dried in the vacuum desiccator for 24 hours and thereafter, the next test was performed.

<Measurement of Radial Force>

The radial force of the prepared stent was measured by the stent radial force measuring jig and the tensile strength tester (UTM).

The radial force measuring equipment is schematically illustrated in FIG. 1 given below.

1) The jig for measuring the stent radiation force was installed in the tensile strength tester.

2) The calibration was performed in order to adjust the diameter of the radiation force measurer with the system.

3) The length information of the stent was input into the system and thereafter, the stent was contracted up to 1.5 mm and the graph thereof was recorded. The result is shown in FIG. 14.

As an exemplary embodiment of the present invention, the external appearance of the stent after the shape memory extending process is schematically illustrated in FIG. 11.

Further, as an exemplary embodiment of the present invention, the external appearance of the stent after the crimping process is schematically illustrated in FIG. 12.

In addition, as an exemplary embodiment of the present invention, the external appearance of the stent after the balloon extending process is schematically illustrated in FIG. 13.

Moreover, a change of the outer diameter (mm) for each process of the Example of the present invention is shown in Table 11 given below.

TABLE 11

| | Before shape memory extension | After shape memory extension | Crimping | Balloon inflation |
|---|---|---|---|---|
| J1 | 3.45 | 5.00 | 1.80 | 3.35 |
| J2 | 3.45 | 5.00 | 1.80 | 3.34 |
| J3 | 3.45 | 5.00 | 1.80 | 3.36 |

Further, the radial force measurement results of the Example of the present invention are shown in Table 12 given below.

TABLE 12

| | | Radial force at 1.5 mm (mbar) |
|---|---|---|
| Example | J1 | 3179 |
| | J2 | 3366 |
| | J3 | 3854 |

Like the result, according to the present invention, an effect of shape memory extension can be achieved, in which radial force of the biodegradable stent largely increases through the shape memory extending process and the number of cracks decreases after the balloon extends and the outer diameter of the biodegradable stent is controlled and extended by means of the crimper while applying pressure to the balloon and a molecule array state of a polymer is changed.

The balloon catheter may be divided into three types according to the balloon compliance. A balloon of which a change rate from a minimum diameter to a maximum diameter of the balloon is in the range of 5 to 10% is a non-compliant balloon, a balloon of which the change rate from the minimum diameter to the maximum diameter of the balloon is in the range of 15 to 30% is a semi-compliant balloon, and a balloon of which the change rate from the minimum diameter to the maximum diameter of the balloon is in the range of 50 to 600% is a compliant balloon. In the present invention, when the compliant balloon in which a change of an outer diameter of the balloon is not limited during shape memory extension is used, the stent can be uniformly extended by using a balloon which is not folded and an effect of an increase in radial force and a decrease in the number of cracks is improved through uniform extension of the stent.

The invention claimed is:

1. A shape memory extending method of a biodegradable stent, comprising:
   providing a stent made of a biodegradable polymer on an external surface of a balloon of a first balloon catheter;
   extending an outer diameter of the stent by applying a first pressure to the balloon of the first balloon catheter to produce a stent with an extended outer diameter;
   providing the stent with the extended outer diameter on an external surface of a balloon of a second balloon catheter; and
   reducing the extended outer diameter of the stent, by crimping the stent while applying a second pressure to the balloon of the second balloon catheter;
   wherein the step of extending the outer diameter of the stent is conducted at a temperature range of 55 to 180° C.; and
   wherein the second balloon catheter is provided in crimping equipment.

2. The shape memory extending method of a biodegradable stent of claim 1, wherein each of the first balloon catheter and the second balloon catheter is independently provided in crimping equipment.

3. The shape memory extending method of a biodegradable stent of claim 1, wherein the stent made of the biodegradable polymer is a stent acquired by laser-cutting a biodegradable polymer tube.

4. The shape memory extending method of a biodegradable stent of claim 1, wherein each of the first balloon catheter and the second balloon catheter is independently a compliant balloon catheter or semi-compliant balloon catheter.

5. The shape memory extending method of a biodegradable stent of claim 4, wherein the first balloon catheter is the compliant balloon catheter and the second balloon catheter is the semi-compliant balloon catheter.

6. The shape memory extending method of a biodegradable stent of claim 5, wherein the first balloon catheter is the compliant balloon catheter in which a balloon is not folded or the second balloon catheter is the semi-compliant balloon catheter in which the balloon is folded.

7. The shape memory extending method of a biodegradable stent of claim 1, wherein the step of reducing the extended outer diameter of the stent is conducted at a temperature range of 37 to 80° C.

8. The shape memory extending method of a biodegradable stent of claim 1, wherein the first pressure and the second pressure is each independently in the range of 1 to 350 psi (0.06 to 23.8 atm).

9. The shape memory extending method of a biodegradable stent of claim 1, wherein the biodegradable polymer is selected from the group consisting of polyglycolide, polylactide, poly p-dioxanone, polycaprolactone, trimethylene carbonate, polyhydroxyalkanoates, polypropylene fumarate, polyortho esters, polyester, polyanhydride, polyphosphazenes, polyalkylcianoacrylatepoloxamers, polyamino L-tyrosine, modified polysaccharides, oxidized cellulose, gelatin, and collagen.

10. The shape memory extending method of a biodegradable stent of claim 1, wherein in the extending of the outer diameter of the stent, the outer diameter of the stent is changed by 105 to 500% based on the outer diameter of an initial stent.

11. The shape memory extending method of a biodegradable stent of claim 1, wherein in the reducing of the extended outer diameter of the stent, the outer diameter of the stent is changed by 10 to 50% based on the outer diameter of the stent which is maximally enlarged.

\* \* \* \* \*